Figure 1:
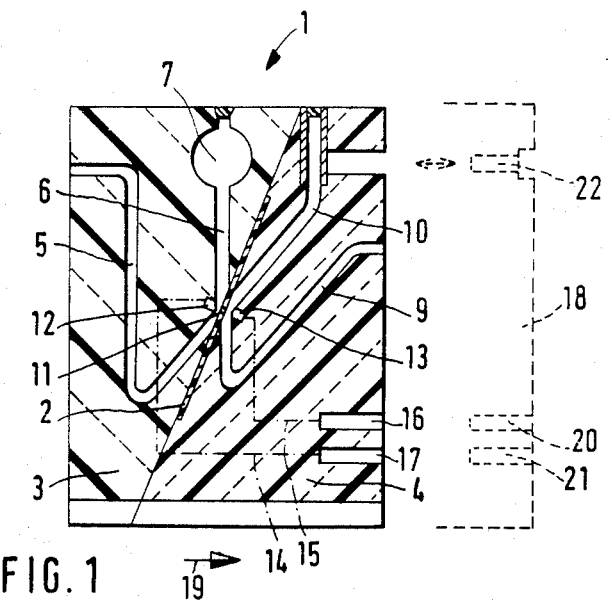

United States Patent [19]

Kiesewetter et al.

[11] Patent Number: 4,521,729
[45] Date of Patent: Jun. 4, 1985

[54] INSTRUMENT FOR MEASURING THE DEFORMING CAPACITY OF RED BLOOD CORPUSCLES

[76] Inventors: Holger Kiesewetter, Schneebergweg 211, D-5100 Aachen; Heinz Myrenne, Steffensgasse 9, D-5106 Roetgen; Hans-Gunther Roggenkamp, Kullenhofstrasse 36, D-5100 Aachen, all of Fed. Rep. of Germany

[21] Appl. No.: 489,672

[22] Filed: Apr. 28, 1983

[30] Foreign Application Priority Data

Apr. 28, 1982 [DE] Fed. Rep. of Germany ....... 3215719

[51] Int. Cl.³ ............................................. G01N 27/00
[52] U.S. Cl. ................................................... 324/71.1
[58] Field of Search ............................ 324/71.1, 71.4; 73/61.4; 368/89, 107; 377/10–12; 364/555; 128/632, 635, 637, 734, 774

[56] References Cited

U.S. PATENT DOCUMENTS 4,240,029 12/1980 Haynes .................................. 377/12
4,348,890 9/1982 Hanss ................................... 73/61.4
4,375,615 3/1983 Haynes .................................. 377/11
4,402,216 9/1983 Peterson ............................... 73/61.4

Primary Examiner—Michael J. Tokar
Assistant Examiner—Kevin D. O'Shea
Attorney, Agent, or Firm—Cushman, Darby & Cushman

[57] ABSTRACT

For measuring the deformation capacity of erythrocytes use is made of a sample vessel that is walled off into two spaces by a piece of foil with a pore therein. One such space is filled with buffer solution with erythrocytes and the other is filled with buffer solution without erythrocytes. A pressure head is produced acting across the foil for causing transit or passage of the erythrocytes through the opening, whose diameter is less than the major quiescent diameter of an erythrocyte so that information on the deformation capacity may be produced by measuring the transit time. This is done by electrodes placed on the two sides of the opening so that changes in the resistance to alternating current by an erythrocyte in transit may be sensed and the transit time taken. After about 200 transits the readings are processed in a processing unit.

22 Claims, 3 Drawing Figures

INSTRUMENT FOR MEASURING THE DEFORMING CAPACITY OF RED BLOOD CORPUSCLES

BACKGROUND OF THE INVENTION

The present invention is with respect to an instrument for measuring the deforming capacity of erythrocytes having at least one sample vessel that is walled off by a foil into two vessel spaces, the foil having a sample flow opening, whose diameter is less than the major quiescent diameter of an erythrocyte, a first one of said vessel spaces being designed to take up a buffer solution together with erythrocytes so that there is a pressure gradient between the two vessel spaces towards the second vessel space (in which there is buffer solution free of erythrocytes) producing a flow between the first and second spaces through the said opening.

An important parameter for the flow behavior of blood is the capacity of the erythrocytes to undergo deformation. In the large blood vessels this deformation is an adaptation of the erythrocytes to the hydrodynamic forces, that is to say to make the hydrodynamic resistance as low a possible, while in small blood vessels it is a question of adaptation to the geometrical limitations. In the last few years wide-ranging basic research has been undertaken on the cause and effect of the deformation capacity of the erythrocytes, which do not have nuclei, of the blood of man and other mammals, such work having made it clear that the normally high ability to flow of the blood at a high speed through the finest blood vessels is dependent on the deformation capacity. In this respect the deformation capacity is greatly dependent on the mechanical properties of the erythrocytes, such properties in turn being controlled by structure and chemical make-up thereof.

An erythrocyte may be looked upon as a membrane sac, that is incompletely filled with liquid and whose size is species-specific and is not dependent in any way on the size of the body. The mean diameter of the humane erythrocytes is 7.5 microns with a height of about 1.5 to 2 microns. The volume is 85 to 90 cubic microns and the surface area somewhere between 120 and 160 square microns. On average there are about 25 trillion erythrocytes present in the circulating blood, that have an overall surface area of 3000 to 4000 square meters.

If one were to take it that an erythrocyte has a volume of 90 cubic microns and a spherical form, the ratio between the surface area and the volume of the erythrocytes would then be about 1.07. However the real ratio is between 1.3 and 1.8. Because of the deformation capacity of the membrane sac and the viscosity of the liquid therein, an erythrocyte is in a very good position with respect to changing its outer form in keeping with the forces acting on it. The main purpose of the erythrocytes is the transport of oxygen to the ultimate user, that is to say every parenchyma cell, and to take up carbon dioxide as a product of metabolism from such cells. This purpose may only be effected by the erythrocytes if they are in a position to make their way along the nutritive capillary bed with its tubes that have a diameter of 3 to 5 microns, that is to say smaller than the diameter of the erythrocytes themselves within a reasonable time. On the footing of this simple geometrical limiting condition one may at once see the importance of the deformation capacity of the erythrocytes with respect to the flow properties in the nutritive capillaries in all the organs of the body. Different diseases have effects on the deformation capacity of the erythrocytes so that measuring the properties of erythrocytes with a limited deformation capacity may make diagnosis of disease processes possible.

The nutritive capillaries and more specially the splenic sinuses are responsible for filtering out erythrocytes no longer having a good deformation capacity so that the time that these erythrocytes are kept in the blood circulation is quite limited. It may be seen from that only a specially sensitive measuring method and measuring instrument would have the power of sensing the minute or discrete changes in the deformation capacity of erythrocytes. On the one hand, when measuring the deformation capacity or deformability, one purpose is that of copying the geometry and the hydrodynamics of the microcirculation as far as possible while, on the other hand, seeing that the measuring operation itself has no or only the least possible effect on the simulation of microcirculation conditions.

GENERAL OVERVIEW OF KNOWN MEASURING METHODS AND INSTRUMENTS.

To give a full picture of the background of the invention details will be given of some six known methods.

1. Viscosity measurement in rotary or capillary viscosity meters. In this measuring process washed erythrocytes are used in saline solutions buffered to pH 7.4 in the form of a suspension, because the cell deformation capacity is indirectly measured. If autologous plasma or another suspension medium is used containing particles making possible aggregation of the erythrocytes, then on using such a suspension it will not only be the deformation capacity of the erythrocytes but furthermore the effect of cell aggregation on the viscosity that will be measured. When such measurements are undertaken the degrees of shear are so high that it is only the behavior of the erythrocytes under high speed flow conditions that are simulated, the erythrocytes then behaving like drops of liquid adapting their form to the conditions of flow and the erythrocyte suspension then coming to have the properties of an emulsion. The deformation in a microcirculation is however an adaptation to a given geometry so that any attempt made at measuring the deformation capacity in the capillaries by measuring the viscosity in the capillaries will only give rough readings.

2. Measuring the geometry of the erythrocytes in a defined shear field. The outer form of the erythrocytes is photographed in a high vicosity suspension medium in which they are under the effect of a flow field. However, not one of the known methods may be said to give anything like the true picture of the conditions in the microcirculation.

3. Measuring the packing density of erythrocytes at given force levels. In this way of measuring, the packing density of erythrocytes is measured after being centrifuged. However overly great, that is to say unnaturally high, forces and not true physiological forces then take effect on the erythrocytes. Another point is that this method may be said to be based on the false assumption that readings for the sedimentation speed taken while centrifuging in giant centrifuges with low centrifugal forces will be representative of the deformation capacity, whereas in fact the sedimentation speed is mainly dependent on aggregation.

4. Aspiration of a defined part or of whole erythrocytes in micropipettes. The aspiration vacuum ($5 \times 10^4$ Pa) used in a tube with a diameter of 1 micron is unnaturally high, that is to say unphysiological. Although on using a tube with a inside diameter of 3 microns the pressures are in the natural, physiological range (30 Pa) the process becomes very slow if measurements are taken on a representative number of cells and it may not be used for routine measurements.

5. Filtration of erythrocyte suspensions or anticoagulated entire blood under different defined limiting conditions. Methods of filtering for testing the deformation capacity of erythrocytes are known using filters such as pore sieves or felt-like diaphragms with capillary gaps, in the case of which the driving pressure or the filtered volumetric flow is measured. Mostly the driving pressures are overly high so that the thrust forces acting on the erythrocytes are overly high as well. A further error in the method may be seen in the use of entire blood, because the filters used become stopped up in a way dependent on the numbers of leucocytes and thrombocytes so that it is not simply the deformation capacity of the erythrocyte that is measured but, in addition, the further effect of the decrease with time of the number of pores in the filters. A further point common to all methods using filtration is more specially the fact that measuring takes place integratively. That is to say, for a given reading for the filtered volumetric flow it is not possible to see if, for example, the overall cell population has been damaged to a small degree or if the greater part of the erythrocytes has a normal power of deformation and only a small part of the population has to a high degree lost the power of deformation.

6. Measurement of the time taken for single erythrocytes to make their way through a hole in a single hole diaphragm. This known method (see Scan. J. clin. Lab. Invest., 41, Suppl. 156, 1981) is used for measuring the deformation capacity of single erythrocytes by timing them as they go through a single pore while keeping to certain limiting geometrical and hydrodynamic conditions, mirroring those in a microcirculation. The important point about this method is causing flow through a single flow opening (pore) in a piece of plastic foil, that is looked upon as a model of a natural capillary. The pore diameter is in this respect smaller than the quiescent diameter of the erythrocytes and is in a range of 3 to 6 microns, the length of the pores being in a range of 15 to 200 microns. In this known process an optical measuring instrument is used for timing the single erythrocytes on their way through the pore. In this respect it is necessary to have a sample vessel of material transparent to light that is walled off into two spaces by a diaphragm, the two spaces being joined up with each other by the pore in the said diaphragm. A suspension with cells whose deformation capacity is to be measured, is put in the sample vessel and forced through a pore by an adjustable pressure. The optical measuring instrument is designed on the same lines as a microscope with the surface of the diaphragm in the focussing place of an illuminating beam. The part of the illuminating light pencil that is directed through the pore, is detected and amplified by a photomultiplier to give an electrical signal. Every time an erythrocyte is in the act of moving through the pore, this part of the light pencil or beam, named the detecting beam, is partly cut off or attenuated for all the time that the erythrocyte is in the pore, that is to say the time the light is partly cut off is the same as the time in which the erythrocyte is in the pore. For processing this pore transit or passage time measured for one erythrocyte after the other, the signal from the photomultiplier is sent to a microprocessor.

The known optical instrument for measuring the transit times of single erythrocytes through a pore is complex, not the least reason for this being the adjustments that have to be done on the optical system. In fact, this optical instrument is best fitted for scientific work in large laboratories with highly experienced staff and is less useful for screening tests, for example, or for use in clinics because of the complex nature of the apparatus and the way of running it.

7. Further systems for measuring the parameters of blood corpuscles are noted in the German Offenlegungsschrift specification No. 2,405,839 and in Nachrichtentechnik Vol 12, 1962, no 2, pages 47 to 50.

The German Offenlegungsschrift specification No. 2,405,839 is with respect to a system for measuring the flexibility of blood corpuscles, in which the later are made to go through a measuring duct in a metal diaphragm, the measuring operation itself being optical. In such optical measuring processes a number of artifacts are likely, as for example one caused by shaking of the apparatus which makes it seem that corpuscles are moving through the duct, or random upward and downward oscillation of the single erythrocytes which will give false readings for the transit times, and so on.

The apparatus of which there is an account in the periodical "Nachrichtentechnik" is a form of Coulter measuring apparatus for counting particles of a suspension and measuring their size using a flow-through pore whose size is of the same order as the size of erythrocytes but is mostly made markedly larger, because in this measuring method the capacity for deformation of the particles is not to have any effect on the measurements because it would give undesired effects and would even have to be corrected by a form factor.

Furthermore in this apparatus the erythrocytes are in a direct current. The erythrocytes are electrically charged particles so that they are acted upon by a force whose size may hardly be controlled. The force undergoes changes from one blood sample to the next one so that standardized measurements under defined conditions may not be taken.

A further point is that on using such a direct voltage, electrolytic effects are caused in the suspension medium and denaturing effects are caused in the membrane protein because of the overgreat heating effect caused by the flow of current. This may only be put up with in the Coulter measuring apparatus.

GENERAL OUTLINE OF THE INVENTION

Taking this prior art into account it may be said that one purpose of the invention is that of designing an instrument for measuring the deformation capacity of red erythrocytes, that is simple in design and may be simply used.

For effecting this purpose and further purposes that will become clear on reading further parts of the present specification, an instrument for measuring the deformation of erythrocytes in keeping with the present invention is characterized in that on the two sides of the foil walling off the sample vessel into two spaces there are two electrodes and there is furthermore a voltage measuring instrument for measuring a voltage change at the electrodes, for measuring and sensing for a length of time the change in voltage at the electrodes caused by the motion of an erythrocyte making its way through the said flow opening or pore.

The time in which there is a change in the voltage may be seen to be equal to the transit time of an erythrocyte through the flow opening. Such a measuring instrument may be simply and cheaply manufactured and because the use thereof is simple, there is hardly any chance of wrong operation thereof. This being so, it is quite well fitted for use in clinics, medical practices and for screening tests.

Further useful developments of the invention will be seen from the claims and the detailed account of a working example thereof.

LIST OF DIFFERENT VIEWS OF THE FIGURES

Figure 2:
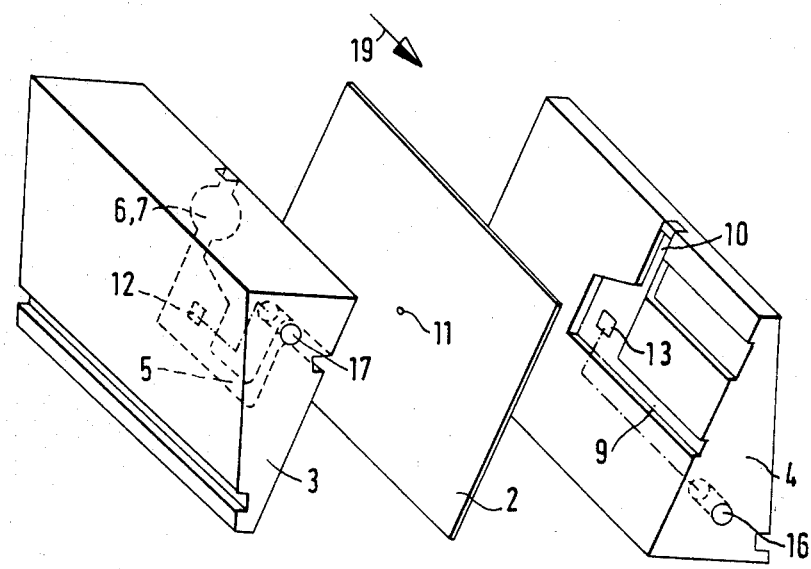
Figure 3:
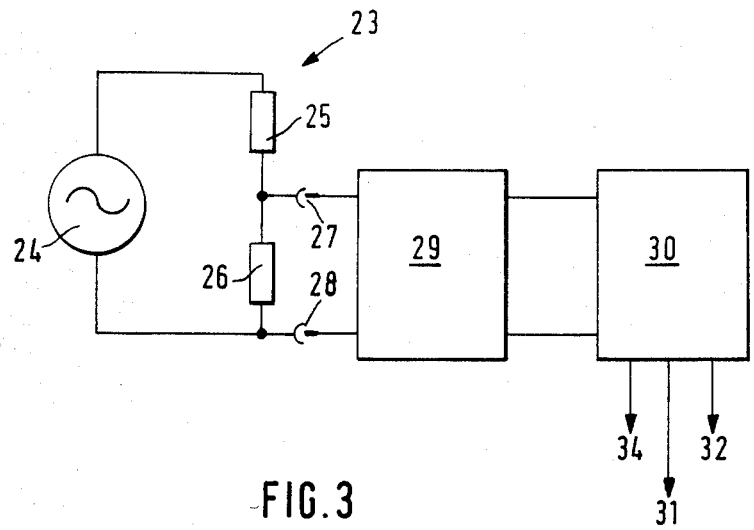

FIG. 1 is a diagrammatic section of a sample vessel.
FIG. 2 is an exploded view of the sample vessel.
FIG. 3 is a diagram of an electrical measuring instrument.

DETAILED ACCOUNT OF WORKING EXAMPLE OF THE INVENTION

In FIG. 1 the reader will see a sample or measuring vessel 1 whose inner space is walled off by a piece of foil 2 into a first space 2 and a second space 4. The first vessel space 3 is formed by an inlet duct 5 running out sideways and then straight downwards before again changing in direction in an upward direction, by an upwardly running duct 6 and by an erythrocyte reservoir that may be joined therewith. The second vessel space 4 is formed by an outlet duct 9 and a cleaning duct 10, the outlet duct 9 running on the level from the side of the vessel 1, it then turning downwards and then turning upwards again at the foil 2. The part of the outlet duct 9 on the level is in this respect lower than the part on the level of the inlet duct 5. The foil 2 has a pore 11 or flow through opening in the part thereof forming a wall between the first and second vessels spaces 3 and 4. On the two sides of the pore 11 there are the electrodes 12 and 13, that is to say one to each side of the foil. The electrodes are joined by way of electrical conductors 14 and 15 with sockets 16 and 17 for plugs. The sample vessel may be pushed into a housing 18 (marked with in broken lines) and moved in the direction of the arrow 19 towards a connection part. The connection parts are more specially the plug contacts 20 and 21, that are joined up with an electrical measuring instrument (FIG. 2) and a coupling 22 joining up with the cleaning duct 10, that is joined up by way of a flexible pipe with a generator for producing a pressure shock wave.

In FIG. 2 the reader will see a measuring vessel manufactured in keeping with the diagram of FIG. 1. In this vessel the separating wall is in the form of the foil 22 placed between the two parts of the vessel, that are best joined together by adhesive.

FIG. 3 is a block schematic of the electrical measuring instrument. There is a circuit 23 made up of an a.c. source or generator 24, an input or ballast resistor 25 and a pore resistor 26. The pore resistor has a valve equal to the resistance between the two electrodes 12 and 13 by way of the pore 11 to be seen in FIG. 1. The connection points 27 and 28 on the pore resistor 26 are marked as the terminals on the plug sockets 16 and 17 and on the other hand the electrical wires 14 and 15 in FIG. 1. A measuring and matching unit 29 is joined up with the connection points 27 and 28 in the one case and the electrodes 12 and 13 (FIG. 1) in the other case. The output of the unit 29 is joined up with a processing unit. The measuring and matching unit 29 is made up mainly of a voltmeter, having a signal output, for giving readings for changes in voltage at the pore resistor 26, and an analog-digital converter, for turning readings, in the form of electrical signals, into a form of signal that may be processed in the processing unit 30. The processing unit has a microprocessor for statistically processing the changes at the pore resistor, a connection 31 for a display and a plotter terminal 32. The processing unit 30 further has a timer or time limiter that has a connection 34 for joining it up with a cleaning unit (not figured) that is joined up with coupling 22 as seen in FIG. 1.

An account will now be given of the sample vessel 1 in connection with the electrical measuring apparatus. To take a reading only one drop of blood is needed that may best taken from the patent's ear lobe or from the finger tip. This being possible simply and only using a needle, there is no need for a doctor to be present and the blood may be taken by a nurse for example. The drop of blood is then taken up in micropipette or the like and suspended in a buffer solution in an anticoagulated or non-anticoagulated condition. Nextly the suspension is filled by way of the inlet duct into the sample vessel. If the reading is to be taken in plasma or serum and not in a buffer solution, then it is necessary to take a large amount of blood (about 8 ml.) from a vein. Pure plasma is produced therefrom by centrifuging and a drop of blood is suspended therein. The hematotocrit valve is adjusted artificially not only in the buffer but furthermore in the plasma to about 1%.

The design is such that the inlet duct 5 is so placed in relation to the outlet duct 9 that there is a hydrostatic head or pressure difference between the first vessel space 3 and the second vessel space 4, that is responsible for there being a flow of buffer solution and erythrocytes through the pore 11. The foil 2 is placed at an angle of roughly 65 deg., this giving the useful effect of stopping sedimentation of the erythrocytes on the foil 2 and stopping them from moving irregularly through the pore. In fact with the said angle, there will be a regular downward rolling motion into the pore of the said erythrocytes. The best angle of the foil 2 is 55 to 56 deg. and in any case within a range of 45 to 80 deg.

Because of this design, once the drop of blood has been placed in the sample vessel 1 the motion of the erythrocytes through the pore 11 will be started. The measuring operation as such is however only started after the measuring vessel 1 has been placed in the housing 18. On doing this the plug sockets 16 and 17 and the plug contacts 20 and 21, the measuring vessel 1 and the electrical measuring apparatus are joined up together. The general idea of the measuring operation is based on the fact that the electrical resistance between the electrodes 12 and 13 is changed every time an erythrocyte goes through the pore 11. The erythrocytes may be timed as they do this and from the time reading the deformation capacity of the erythrocytes may be seen. For measuring the change in resistance the electrodes 12 and 13 are supplied with an alternating voltage from the a.c. source 24. The frequency of this alternating voltage is in a range of 1 kHz to 100 kHz and more specially between 5 kHz and 20 kHz. The alternating voltage, that is supplied through the input resistor 25 and the pore resistor 26 has a peak amplitude in a range of 5 to 100 mV and more specially 10 mV to 40 mV. The value of the input resistor 25 is of the same order as that of the pore resistor 26 (in order to get the largest possible changes in the signal when erthyrocytes make their way through the pore) and is in a range of 10 kilo-ohms to 10 megohms and more specially 100 kilo-ohms and 2 megohms. Unlike a system in which the transit of the erythrocyte through the pore is measured with d.c., the method with a.c. used here makes certain that there is no change in the transit time caused by electrophoresis. Furthermore the heating effect caused in the pore 11 by the current flowing through the pore 11 when measuring is taking place, is cut down as far as possible because the voltage or potential difference, on which the current value is dependent, is low (1 mV to 20 mV as measured across the pore 11). The heating effect is in fact kept down to a value under $10^{-10}$ deg. C, that is generally speaking quite safe from the point of view of accuracy of measurement. All in all the outcome of this is that the transit of the erythrocytes through the pore 11 is practically not dependent in any way on the measuring operation, or in other words the speed of the erythrocytes would be quite the same as if there were no flow of electricity.

The placing of the electrodes 12 and 13 is generally not critical, as for example with one in the inlet and one in the outlet duct 5 and 9. However it is best if they are not placed near the foil 2, that is to say under and over the pore 11, the size of the electrodes hardly playing an important part. However they are to be made large enough to see that the transmission resistance between the electrode and the liquid is very much smaller than the resistance of the chain of measuring component (that is to say the input resistor 25 and the pore resistor 26) and that no air bubbles are formed on the electrodes with an insulating effect. Good results have been produced with electrode areas in a range of 3 to 14 sq. mm.

In connection with measuring using a.c. it is to be kept in mind that the foil itself has the effect of a capacitor so that in addition to the ohmic pore resistance there is a parallel capacitive resistance. With an increase in the frequency and for this reason with an increase in the resolution of the transit times the value of the capacitive resistance goes down and from this it will be seen that when the frequency at which reading are taken is increase the change in the change in the signal on erythrocyte transit will go down. However if one keeps to the values given for the components herein, the design of the apparatus will be in line with the purpose in hand and there will be the useful effect that the readings are hardly changed at all by the function of the apparatus.

As for the size of the sample vessel 1, values that have turned out to be in order are: for the diameter of the pore, between 3 and 6 microns; for the length of the pore, 15 to 200 microns; for the pressure head across the pore 11, less than 100 Pa; and for the hematocrit value (volume of the erythrocytes), about 1%.

The change in resistance produced by the transit of an erythrocyte through the pore 11 is timed by the measuring and matching unit 29 and the reading sent to the processing unit 30. After a given number of transists, more specially 200 transits, the measuring operation is stopped and the statistical processing of the stored original list (data in the memory) is undertaken. By pushing on a button (producing a reading command) the user of the apparatus is then given the result. The results of the measurement may for example be the median value (transit or passage time at which 50% of the transists will have taken place), The standard deviation as a measure for the homogeneity of the sample, and the number of passages that are greater than a given time as for example 200 msec. and in each case are representative of an occlusion of the pore 11, such results being presented to the user on a digital readout or in a printed form. The word occulsion is used herein in the sense of a transit at a speed less than is necessary for a high enough rate of supply of oxygen to the body tissues. For cleaning the pore if it becomes stopped up in a measuring operation by a particle there is the automatically working clearing unit (not figured) which on a transit time greater than the said upper limit of for example 200 msec being sensed by the measuring unit 29, gets a cleaning pulse, that is translated by it into a pressure surge wave acting on the foil 2 that has the effect of forcing the particle out of the pore 11 again. It is with this connection as well that there is a good reason to have the foil 2 placed at an angle inasfar as any particle blocking the foil 2, will safely be moved on in a downward direction after it has been forced out of the pore and it will not have any further effect on the measuring operation.

The time needed for running the test, that is to say the time from the taking of the blood sample to the giving of output readings as the result of the test is less that 5 minutes. The measuring may be undertaken using any desired physiological suspending medium. In this respect the hematocrit value is to be about 1% by vol to make certain that there is never more than one erythrocyte in the pore 11 at one and the same time. The effect of aggregation, that may be important in the case of suspending mediums such as autologous plasma or serum, on the distribution of the erythrocyte transit times may be separately recorded and if desired compensated by recording double transits, that is to say the transit of a pair. For routine measurements a standard suspending medium may be used and the washed (or better unwashed) erythrocytes may be suspended in it, This suspending medium does not in this respect have any marked effect on the deformation capacity of the erythrocytes; furthermore it makes it possible for them to be stored for a relatively long time and generally puts an end to aggregation.

In addition to the measurement of the transit or passage time of the erythrocytes and the recording of double transits the third factor measured is the number or rate of occlusions. Herein the word occlusion is used in the sense of a transit time that is greater than a given or preselected time, as for example 200 msec. On the footing of the occlusion rate and of the average value of the transit times and by changing the pore diameter the pore length and the driving pressure head it is possible with this measuring apparatus to make a selection of the different factors having an effect on the deformation capacity and on the basis of the readings produced to make a decision about any specific treatment of the patient that may be needed in a given case.

The parameters that have turned out to be selectable are the surface area to volume ratio, the viscosity of the cytoplasma, the stiffness of the membrane and the rotation of the membrane about the cell content. For distinguishing these values it is necessary to take a number of readings with the same erythrocyte suspension with different pore diameter, pore lengths and/or different driving pressure heads. This may best be done using an apparatus with a number of sample vessels placed in parallel. In fact with an increase of the surface area to volume ratio over 1.1 there is a marked and quite significant increase in the occlusion rate and it goes up towards 100%. If the cell membrane is stiffened, the transit or passage time will be increased a little, whatever the pore diameter, while the occulsion rate will be significantly stepped up with a decrease in the pore diameter.

On an increase in the viscosity of the cytoplasma the transit times and the occlusion rate will be markedly greater. If the rotation of the membrane about the cell contents is decreased there will be a significant increase in the transit time whatever the pore diameter, while the occlusion rate is kept more or less unchanged.

To make it possible for the blood to be tested in the way noted under different limiting conditions or for a number of different blood samples to be tested at the same time, the measuring instrument to be seen in the figures herein may be designed as a multi-channel version. Such a form of the apparatus has as its main parts a compact housing, the electrical system and a number of sample vessels, for example 8 such vessels. The sample vessels are best designed with thermostats so that the samples are tested under the same conditions in each case. These vessels may be designed, as noted earlier herein, in the form plug-in units, that are pushed onto plug contacts in the housing, This gives a useful effect inasfar as the sample vessels may then simply be pulled out for cleaning and there is no wiring as such between a sample vessel and the rest of the apparatus.

The sample vessels may be manufactured of any non-conducting material not reacting with blood, the preferred material being clear or transparent polyurethane. The electrodes have to be made of noble electrode materials such as stainless steel, titanium, gold, or silver or have to be plated with such materials. In addition to manufacturing a sample vessel using replaceable plastic foil, it is furthermore possible for the sample vessel to be cast and to have foil bonded therein and in this case it is only used once. Furthermore the pressure gradient might be produced by a system producing a differential pressure or by a system with pressure regulation in place of the hydrostatic system detailed hereinbefore.

For simple routine measurements, as for example in physicians practices, the apparatus may be manufactured with one channel, the sample vessel being able to be placed in a housing so that on shutting a housing door the measuring operation would be automatically started. In this case the sample vessel might well be made in the form of a throw-away vessel with a foil lining 2 bonded therein, the vessel being supplied filled with buffer solution so that all the physician would have to do would be the injection of the blood into the vessel.

The pore 11 in the foil 2 is best produced by a method as used in nuclear trace technology and then by wet chemical processing. This makes it possible for the pores to be made regularly and true to size, although however the desired size of the pore diameter and the length will have a tolerance range of ±5%. The system for taking electrical measurements does however make it possible for the transit time readings to be corrected to a standard pore size, that may be fictive, so that it is then more readily possible to make a comparison between the readings. An account will now be given of how the correction is made. The voltage amplitude (U) across a pore 11 is proportional to the pore length and is inversely proportional to the square of the pore diameter (U is roughly equal to $1/d^2$). With an increase in the pore length or with a decrease in pore diameter the voltage measured at the electrodes and the readings for the transit times go up. Because however the tapped voltage (or voltage reading U) is a measure of the form factor $1/d^2$, the reading for the amplitude may be used for a simple correction of the transit times.

A still better if somewhat more complex correction of the transit time readings is possible if the pore length is electrically measured by measuring the capacitance of the system made up of the two bodies of liquid with the foil therebetween. And then it will be possible, if one keeps to the same buffer solution, for the pore diameter to be worked out from the formula U roughly equal to $1/d^2$ so that then, using form example a calibration table made part of the program, it will be possible to make a correction for the transit time readings for the values, that are now known, of the pore length and the pore diameter.

For testing for and measuring double and multiple transits, a comparator with a given or prefixed reading level may be used. Seeing that the volume is dependent on the resistance, a pulse height analyser may be used with which the readings may taken for the volume distribution of the particles.

As will have been seen from the detailed account herein, the measuring instrument in keeping with the present invention is characterised by the simple design of its structure and its simple and safe way of operation. Furthermore it may be looked upon a general-purpose apparatus.

We claim:

1. In an apparatus for measuring the deformation capacity of erythrocytes comprising at least one sample vessel, a piece of foil walling said vessel off into two sample spaces, said foil having an opening therethrough for the motion of the liquid placed in the apparatus as a sample, said opening having a diameter smaller that the major quiescent diameter of an erythrocyte, means for producing a pressure head across the said foil in a buffer liquid placed in said vessel for causing a flow of said liquid through said opening, at least two electrodes placed on opposite or different sides of said foil, means for supplying said electrodes with voltage, and a voltage measuring system for measuring changes in said voltage at said electrodes on an erythrocyte making its way through said opening in a transit therethrough, wherein said measuring system times said transit.

2. The measuring apparatus as claimed in claim 1 wherein said electrodes are placed near said flow opening at two ends thereof.

3. The measuring apparatus as claimed in claim 2 comprising a thermostatic heating system for control of the temperature of said vessel.

4. The measuring apparatus as claimed in claim 1 wherein said foil is placed at a slope in said vessel, said slope having an angle of 45 deg. to 80 deg. in said vessel.

5. The measuring apparatus as claimed in claim 1 wherein said sample vessel is in the form of a plug-in unit.

6. The measuring apparatus as claimed in claim 1 wherein said vessel is designed for use once only, said vessel filled with buffer.

7. The measuring apparatus as claimed in claim 1 having more than one such sample vessel and means for taking readings therefrom at the same time.

8. The measuring apparatus as claimed in claim 7 wherein said vessels are different from each other in respect of the size of the diameter of the opening, the length thereof and the means for producing said pressure head across said foil.

9. The measuring apparatus as claimed in claim 1 further comprising a means for producing a pressure surge wave in the sample vessel for clearing a particle out of said opening.

10. The measuring apparatus as claimed in claim 1 wherein said foil has an area in a range of 3 to 30 square mm.

11. The measuring apparatus as claimed in claim 1 having means for the supply of an alternating voltage to said electrodes.

12. The measuring apparatus as claimed in claim 11 wherein said alternating voltage has a frequency in a range of 1 to 100 kHz.

13. The measuring apparatus as claimed in claim 10 having an input resistor for supply of said alternating voltage to said electrodes, the value of the resistor being in a range of 100 kilo-ohms to 10 megaohms, the peak to peak amplitude of said voltage having a value between 5 mV and 100 mV.

14. The measuring apparatus as claimed in claim 1 wherein said opening has a diameter in a range of 3 to 6 microns and a length in a range 15 and 100 microns.

15. The measuring apparatus as claimed in claim 1 further having a control and processing unit joined up with an output of said voltage measuring system.

16. The measuring apparatus as claimed in claim 15 wherein said control and processing unit is designed for recording and statistically processing readings for the transits of erythrocytes through said opening, in a way dependent on time.

17. The measuring apparatus as claimed in claim 16 wherein said control and processing unit has an adjustable limit value, means for the comparison of the transit time of an erythrocyte through said opening with this limit value, and means for sensing an event in which said time is greater than said limit, said event being recorded as an occulsion of said opening, means for cleaning said opening by use of a pressure wave, and switch means for causing operation of said clearing means on such an occlusion event being sensed.

18. The measuring apparatus as claimed in claim 1 designed for measuring said voltage at said electrodes, said apparatus further having means for correction of a reading for the transit of an erythrocyte through said opening in keeping with the voltage amplitude, said correction being to a time for erythrocyte transit through a standard or fictive opening.

19. The measuring apparatus as claimed in claim 1 having means for producing said pressure head across said opening hydrostatically by making the liquid level in one vessel space higher than the liquid level in the other vessel space.

20. The measuring apparatus as claimed in claim 17 having means for translating a reading for the number of occlusions into an output signal with respect to the deformation capacity of an erythrocyte in a measuring operation.

21. The measuring apparatus as claimed in claim 1 wherein said sample vessel is made up of two halves with hollows milled thereinto, said hollows being so placed as to be opposite to each other on putting the two halves of the vessel together face to face that said sample space is formed, said foil being placed between said two halves of said vessel so that edges thereof are gripped between said halves on parts thereof free of said hollows, said foil functioning not only for walling off said sample space into two spaces but furthermore functioning as a gasket between the said halves.

22. The measuring apparatus as claimed in claim 1 comprising further a comparison means with a given adjustable value for testing for double and multiple transits.

* * * * *